United States Patent
Lorenz et al.

(10) Patent No.: US 10,102,347 B2
(45) Date of Patent: Oct. 16, 2018

(54) PATIENT SPECIFIC ANATIOMICAL SKETCHES FOR MEDICAL REPORTS

(75) Inventors: Cristian Lorenz, Hamburg (DE); Sebastian Peter Michael Dries, Hamburg (DE); Steffen Renisch, Hamburg (DE); Jens Von Berg, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 1012 days.

(21) Appl. No.: 13/120,181

(22) PCT Filed: Sep. 17, 2009

(86) PCT No.: PCT/IB2009/054070
§ 371 (c)(1),
(2), (4) Date: Mar. 22, 2011

(87) PCT Pub. No.: WO2010/035183
PCT Pub. Date: Apr. 1, 2010

(65) Prior Publication Data
US 2011/0169864 A1   Jul. 14, 2011

(30) Foreign Application Priority Data
Sep. 26, 2008 (EP) .................... 08165277

(51) Int. Cl.
*G06F 19/00* (2011.01)
*G06T 7/00* (2017.01)
(Continued)

(52) U.S. Cl.
CPC ........ *G06F 19/3487* (2013.01); *G06F 19/321* (2013.01); *G06T 7/0012* (2013.01);
(Continued)

(58) Field of Classification Search
CPC ..... G06T 7/0081; G06T 7/0083; G06T 17/00; G06T 7/0085; G06T 7/0089
(Continued)

(56) References Cited

U.S. PATENT DOCUMENTS 6,240,218 B1 * 5/2001 Michael ............... G06K 9/6203
382/170
6,701,174 B1 3/2004 Krause et al.
(Continued)

FOREIGN PATENT DOCUMENTS

| JP | 2007282945 A | 11/2007 |
| JP | 2008067916 A | 3/2008 |
| JP | 2008079770 A | 4/2008 |

OTHER PUBLICATIONS

L. Rodney Long; Biomedical information from a national collection of spine x-rays: film to content-based retrieval; Medical Imaging 2003: PACS and Integrated Medical Information Systems: Design and Evaluation, 70 (May 20, 2003).*
(Continued)

*Primary Examiner* — Yuehan Wang
*Assistant Examiner* — Michael Le

(57) ABSTRACT

The invention relates to a system for producing a representation of an object in image data, based on a template coupled to a model of the object, the system comprising a model unit for adapting the model to the object in the image data, and a template unit for adapting the template to the adapted model on the basis of the coupling between the template and the model. The template defines a representation of the object which is simpler to interpret than the model. Because the template of the invention is coupled to the model, the position, orientation and/or shape of the template is determined by the model adapted to the object in the image data. Hence, the template is adapted to the image
(Continued)

data. The adapted template is capable of representing the object and its individual characteristics.

20 Claims, 6 Drawing Sheets

(51) Int. Cl.
G06T 19/20 (2011.01)
G06T 7/12 (2017.01)
G06T 7/149 (2017.01)
G16H 15/00 (2018.01)

(52) U.S. Cl.
CPC .............. *G06T 7/12* (2017.01); *G06T 7/149* (2017.01); *G06T 19/20* (2013.01); *G16H 15/00* (2018.01); G06T 2207/10072 (2013.01); G06T 2207/10116 (2013.01); G06T 2207/30012 (2013.01); G06T 2219/2021 (2013.01)

(58) Field of Classification Search
USPC .................. 345/619–689, 419, 420, 442
See application file for complete search history.

(56) References Cited

U.S. PATENT DOCUMENTS

| 7,050,876 | B1* | 5/2006 | Fu ................... G05B 19/4099 345/420 |
|---|---|---|---|
| 7,583,857 | B2 | 9/2009 | Xu et al. |
| 7,738,683 | B2 | 6/2010 | Cahill et al. |
| 7,949,542 | B2 | 5/2011 | Hamiter et al. |
| 7,952,576 | B2 | 5/2011 | Oyama et al. |
| 7,979,383 | B2 | 7/2011 | Heilbrunn et al. |
| 8,320,651 | B2 | 11/2012 | Vining et al. |
| 2002/0167517 | A1* | 11/2002 | Sato ............................ 345/424 |
| 2002/0180760 | A1* | 12/2002 | Rubbert .............. G06F 19/3437 345/630 |
| 2003/0174891 | A1* | 9/2003 | Wenzel ................. G06T 7/0004 382/209 |
| 2008/0009722 | A1* | 1/2008 | Simopoulos ............. A61B 8/08 600/437 |

OTHER PUBLICATIONS

Claude Kauffmann; Digital radiography segmentation of a scoliotic vertebral body using deformable models; Medical Imaging 1997: Image Processing, 243 (Apr. 25, 1997).*
JP 2007282945A (Machine Translation on Jan. 27, 2017).*
JP 2008067916A (Machine Translation on Jan. 27, 2017).*
JP 2008079770A (Machine Translation on Jan. 27, 2017).*
Long et al: "Biomedical Information From a National Collection of Spine X-Rays:Film to Content-Based Retrieval"; Proceedings of SPIE Medical Imaging:PACS and Integrated Medical Systems, 2003, SPIE, vol. 5033, pp. 1-15.
Qatarneh, S.: "Development of a Whole Body Atlas for Radiation Therapy Planning and Treatment Optimization"; Doctoral Dissertation, Division of Medical Radiation Physics, Karolinska Institute, Stokholm University, 2006, 69 Page Document.
Xu, Z. et al., "A Hierarchical Compositional Model for Face Representation and Sketching". IEEE Transactions on Pattern Analysis and Machine Intelligence, Jun. 1, 2008, IEEE Computer Society, vol. 30, Nr:6, pp. 955-969.
Xu, Z. et al., "a Hierarchical Compositional Model for Face Representation and Sketching". IEEE Transactions on Pattern Analysis and Machine Intelligence, Jun. 1, 2008. IEEE Computer Society, vol. 40, Nr: 6, pp. 955-969.

* cited by examiner

PATIENT SPECIFIC ANATOMICAL SKETCHES FOR MEDICAL REPORTS

FIELD OF THE INVENTION

The invention relates to representing an object in the image data, using a simplified or schematic model of the object, and, in a particular aspect of the invention, to representing the object in a simplified or schematic image.

BACKGROUND OF THE INVENTION

In model-based image data segmentation, results of the segmentation comprise a model adapted to the image data. Such a model typically includes many details. Therefore, when viewing the model adapted to the image data, said model cannot be easily analyzed on a display or in a report. Adapting a simplified model representing and possibly emphasizing an aspect of a structure of interest to the image data is not feasible because a simplified model does not include enough detail to be successfully adapted to the image data. On the other hand, the simplified model which is not adapted to the structure of interest does not include the structure-specific information.

SUMMARY OF THE INVENTION

It would be advantageous to have a system that is capable of adapting a simplified model representing an aspect of a structure of interest to an object in the image data.

Thus, in an aspect of the invention, there is provided a system for producing a representation of an object in image data, based on a template coupled to a model of the object, the system comprising:

a model unit for adapting the model to the object in the image data; and a template unit for adapting the template to the adapted model on the basis of the coupling between the template and the model.

The template defines a representation of the object which is simpler to interpret than the model. The template may be arranged to emphasize interesting features of the object. The template comprises substantially fewer degrees of freedom and thus can be efficiently adapted to the model. Since the template of the invention is coupled to the model, the position, orientation and/or shape of the template is determined by the model adapted to the object in the image data. Hence, indirectly, the template is adapted to the image data. The adapted template is capable of representing the object and its individual characteristics, e.g., the shape of the object as well as the position and/or orientation of the object with respect to an external, i.e., independent of the adapted model, reference system. Such an external reference system may be defined, e.g., based on the image data.

In an embodiment, the system further comprises an image unit for producing an image of the template. Thus, individual features of the object in the image data described by the template may be further shown in the image produced from the template.

In an embodiment of the system, the template comprises a first portion and a second portion, and the image unit is arranged for producing a first portion of the image, based on the first portion of the template, using a first visual pattern, and a second portion of the image, based on the second portion of the template, using a second visual pattern. Using different visual patterns, e.g. colors or shading, one can easily see how different portions of the object are depicted in the image.

In an embodiment, the template is rigid and is movably coupled to the model. For example, the template may be planar and the plane of the template may be defined by three non co-linear points defined by features of the model. The template unit may be arranged for adapting the planar template to the model such that (i) the plane of the template is determined by the three points of the adapted model, (ii) the center of the template is determined by the mass center of the three points, and (iii) an axis of the template is determined by the line obtained by applying linear regression to the three points of the adapted model.

In an embodiment of the system, the template comprises a plurality of control points which are rigidly or elastically coupled to the model. For example, the positions of the plurality of control points may be based on features of the model. In the case of rigid coupling, the coordinates of the control points are fixed with respect to the model. In the case of elastic coupling, the positions of the plurality of control points are determined by their elastic interaction with the model. The elastic interaction may be described by elastic forces such as harmonic forces. The template may be a curve or a surface defined by the control points using, e.g. interpolation. The skilled person will understand that using non-elastic coupling is, in principle, also possible.

In an embodiment of the system, the template is elastic. For example, the template may be implemented as a mesh comprising a plurality of nodes. The neighboring nodes may interact with each other via elastic forces. Elastic forces are easy to implement and compute. Further, elastic forces properly describe the expected deformation of the template resulting from the deformation of the model of the object. However, a person skilled in the art will appreciate that in an alternative embodiment, some or all nodes may interact with each other via non-elastic forces.

In an embodiment of the system, the template comprises at least one curve or surface. For example, the template may comprise a curve or a surface which is defined, based on a section of the surface model, by a plane.

In a further aspect of the invention, the system is comprised in a reporting system for creating a report, the report comprising the image of the template produced by the image unit of the system.

In a further aspect of the invention, the system is comprised in an image acquisition apparatus.

In a further aspect of the invention, the system is comprised in a workstation. In a further aspect of the invention, there is provided a method of producing a representation of an object in image data, based on a template coupled to a model of the object, the method comprising:

a model step for adapting the model to the object in the image data; and a template step for adapting the template to the adapted model on the basis of the coupling between the template and the model.

In a further aspect of the invention, a computer program product to be loaded by a computer arrangement is provided, the computer program product comprising instructions for producing a representation of an object in image data, based on a template coupled to a model of the object, the computer arrangement comprising a processing unit and a memory, the computer program product, after being loaded, providing said processing unit with the capability to carry out the tasks of:

adapting the model to the object in the image data,
adapting the template to the adapted model on the basis of the coupling between the template and the model.

It will be appreciated by those skilled in the art that two or more of the above-mentioned embodiments, implementations, and/or aspects of the invention may be combined in any way deemed useful.

Modifications and variations of the reporting system, of the image acquisition apparatus, of the workstation, of the method, and/or of the computer program product, which correspond to the described modifications and variations of the system, can be carried out by a person skilled in the art on the basis of the present description.

A person skilled in the art will appreciate that the method may be applied to multidimensional image data, e.g., to 3-dimensional or 4-dimensional images, acquired by various acquisition modalities such as, but not limited to, standard X-ray Imaging, Computed Tomography (CT), Magnetic Resonance Imaging (MRI), Ultrasound (US), Positron Emission Tomography (PET), Single Photon Emission Computed Tomography (SPECT), and Nuclear Medicine (NM).

BRIEF DESCRIPTION OF THE DRAWINGS

These and other aspects of the invention will become apparent from and will be elucidated with respect to the implementations and embodiments described hereinafter and with reference to the accompanying drawings, wherein.

Identical reference numerals are used to denote similar parts throughout the Figures.

DETAILED DESCRIPTION OF EMBODIMENTS

Figure 1:
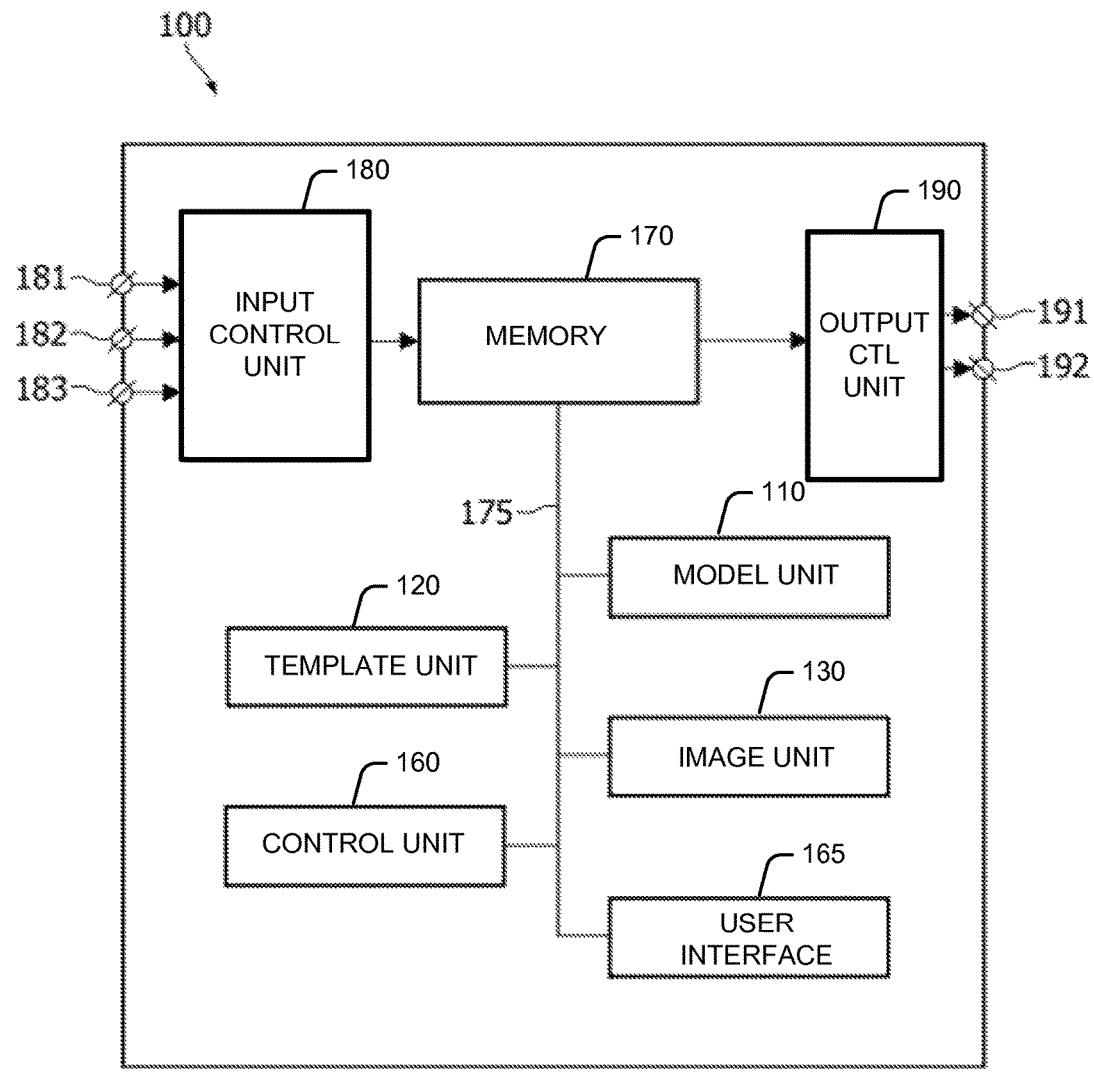
FIG. 1 schematically shows a block diagram of an exemplary embodiment of the system.

FIG. 1 schematically shows a block diagram of an exemplary embodiment of the system 100 for producing a representation of an object in image data, based on a template coupled to a model of the object, the system comprising:
  a model unit 110 for adapting the model to the object in the image data; and
  a template unit 120 for adapting the template to the adapted model on the basis of the coupling between the template and the model.

The exemplary embodiment of the system 100 further comprises the following units:
  an image unit 130 for producing an image of the template;
  a control unit 160 for controlling the workflow in the system 100;
  a user interface 165 for communicating with a user of the system 100; and
  a memory unit 170 for storing data.

In an embodiment of the system 100, there are three input connectors 181, 182 and 183 for the incoming data. The first input connector 181 is arranged to receive data coming in from a data storage means such as, but not limited to, a hard disk, a magnetic tape, a flash memory, or an optical disk. The second input connector 182 is arranged to receive data coming in from a user input device such as, but not limited to, a mouse or a touch screen. The third input connector 183 is arranged to receive data coming in from a user input device such as a keyboard. The input connectors 181, 182 and 183 are connected to an input control unit 180.

In an embodiment of the system 100, there are two output connectors 191 and 192 for the outgoing data. The first output connector 191 is arranged to output the data to a data storage means such as a hard disk, a magnetic tape, a flash memory, or an optical disk. The second output connector 192 is arranged to output the data to a display device. The output connectors 191 and 192 receive the respective data via an output control unit 190.

A person skilled in the art will understand that there are many ways to connect input devices to the input connectors 181, 182 and 183 and the output devices to the output connectors 191 and 192 of the system 100. These ways comprise, but are not limited to, a wired and a wireless connection, a digital network such as, but not limited to, a Local Area Network (LAN) and a Wide Area Network (WAN), the Internet, a digital telephone network, and an analog telephone network.

In an embodiment of the system 100, the system 100 comprises a memory unit 170. The system 100 is arranged to receive input data from external devices via any of the input connectors 181, 182, and 183 and to store the received input data in the memory unit 170. Loading the input data into the memory unit 170 allows quick access to relevant data portions by the units of the system 100. The input data may comprise, for example, the image data. The memory unit 170 may be implemented by devices such as, but not limited to, a Random Access Memory (RAM) chip, a Read Only Memory (ROM) chip, and/or a hard disk drive and a hard disk. The memory unit 170 may be further arranged to store the output data. The output data may comprise, for example, the adapted template data. The memory unit 170 may be also arranged to receive data from and/or deliver data to the units of the system 100 comprising the model unit 110, the template unit 120, the image unit 130, the control unit 160, and the user interface 165, via a memory bus 175. The memory unit 170 is further arranged to make the output data available to external devices via any of the output connectors 191 and 192. Storing data from the units of the system 100 in the memory unit 170 may advantageously improve performance of the units of the system 100 as well as the rate of transfer of the output data from the units of the system 100 to external devices.

Alternatively, the system 100 may comprise no memory unit 170 and no memory bus 175. The input data used by the system 100 may be supplied by at least one external device, such as an external memory or a processor, connected to the units of the system 100. Similarly, the output data produced by the system 100 may be supplied to at least one external device, such as an external memory or a processor, connected to the units of the system 100. The units of the system 100 may be arranged to receive the data from each other via internal connections or via a data bus.

In an embodiment of the system 100, the system 100 comprises a control unit 160 for controlling the workflow in the system 100. The control unit may be arranged to receive control data from and provide control data to the units of the system 100. For example, after adapting the model to the object in the image data, the model unit 110 may be arranged to provide control data "the model is adapted" to the control unit 160, and the control unit 160 may be arranged to provide control data "adapt the template to the model" to the template unit 120. Alternatively, a control function may be implemented in a unit of the system 100.

In an embodiment of the system 100, the system 100 comprises a user interface 165 for communicating with the user of the system 100. The user interface 165 may be arranged to receive a user input for selecting a model and/or a template coupled to the model. The user interface may also provide the user with information, e.g., it may display a view of the adapted template. Optionally, the user interface may receive a user input for selecting a mode of operation of the system such as, e.g., for selecting coupling forces for coupling the template to the model. A person skilled in the art will understand that more functions may be advantageously implemented in the user interface 165 of the system 100.

In an embodiment, the system 100 is employed to model the lumbar vertebra of a patient. The model comprises a deformable mesh model of the lumbar vertebra for adapting to a lumbar vertebra object in CT image data of the patient. Such a model is described, for example, in Tobias Klinder, Cristian Lorenz, Jens von Berg, Sebastian P. M. Dries, Thomas Büllow, Jörn Ostermann: *Automated Model-Based Rib Cage Segmentation and Labeling in CT Images*, MIC-CAI (2) 2007: pp 195-202. The template comprises a contour of the lumbar vertebra. The contour is defined by a planar cross-section of the surface of the lumbar vertebra model and described by a plurality of control points on the surface of the model.

Figure 2A:
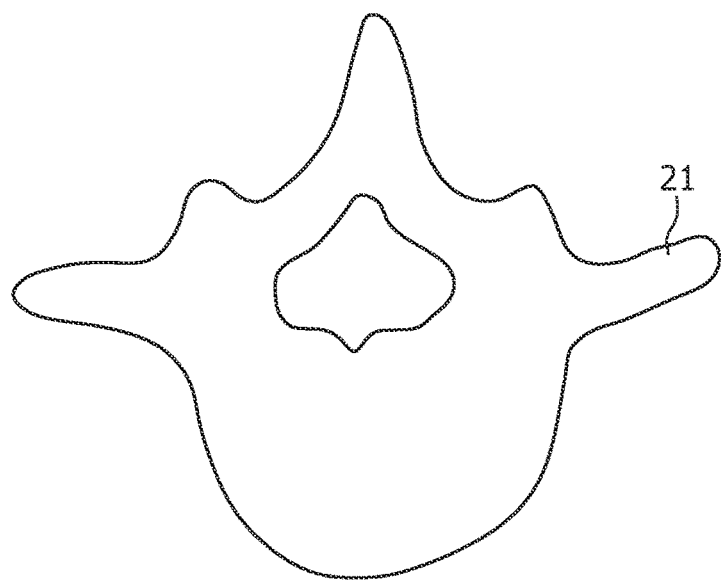
FIG. 2 illustrates the template before (a) and after (b) adaptation by the system.
Figure 2B:
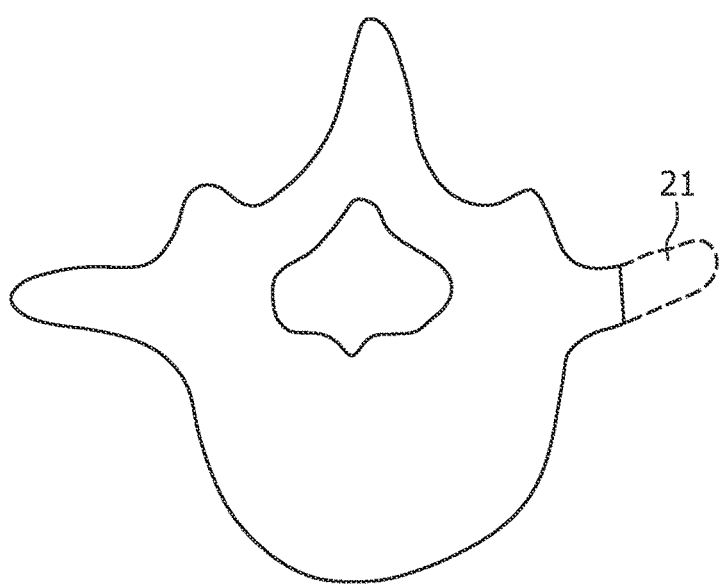
Figure 3:
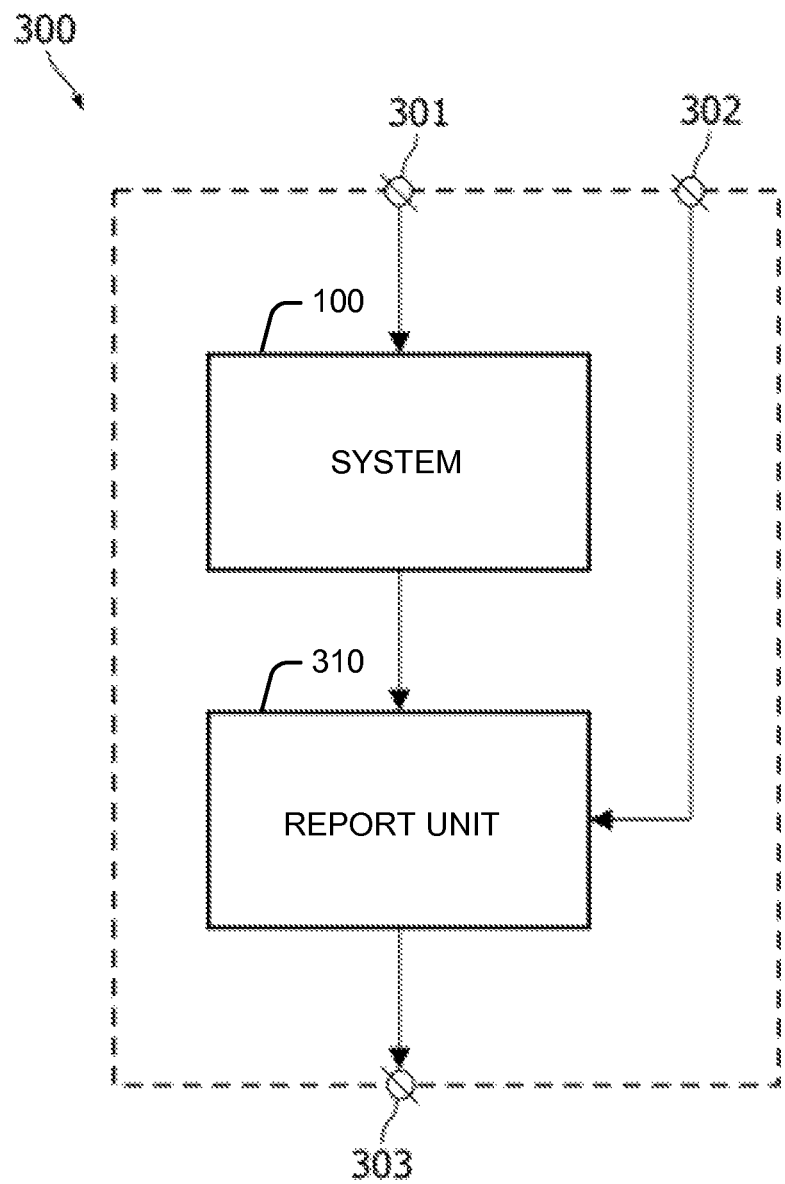
FIG. 3 schematically shows an exemplary embodiment of the reporting system.

After an adaptation of the model by the model unit 110, new positions of the control points of the template contour are found on the surface model of the vertebra by the template unit 120. These control points define the adapted contour of the adapted template. Adapted contours are arranged to take into account individual characteristics of the patient's vertebrae and may show, for example, vertebral compression or fracture. FIG. 2 illustrates an exemplary template of a lumbar vertebra before (a) and after (b) adaptation by the system 100 of the invention. The adapted lumbar vertebra contour illustrates that the lumbar transverse process 21 visible in the template (a) before the adaptation is fractured in the template (b) after the adaptation.

The skilled person will understand that the adapted lumbar vertebra template may be non-planar, because the control points in their new positions on the surface of the adapted model do not need to be coplanar. Thus, in an embodiment, the system 100 further comprises an image unit 130 arranged to produce an image of the adapted template, i.e., a graphical representation of the modeled object. For example, the image may be an orthogonal projection of the adapted template on the plane, computed by minimizing the sum of squares of distances of the control points in their new positions to said plane.

In an embodiment, the system 100 is employed to model the heart of a patient. The model comprises a deformable mesh model of the heart for adapting to a heart object in CT image data of the patient. Such a model and its adaptation is described, for example, in Cristian Lorenz, Jens von Berg, *A comprehensive shape model of the heart*, Medical Image Analysis, Vol. 10, Issue 4, 2006, pp 657-670. The template comprises a surface schematically representing the left ventricle of the heart. The surface is defined by a plurality of control points on the left ventricle surface of the model using, for example, thin spline interpolation. The control points form a subset of the set of vertices of the mesh of the mesh model.

After adaptation of the model by the model unit 110, the new positions of the control points of the template on the surface of the heart model are determined based on the vertex positions of the adapted mesh model. The template unit 120 is arranged to compute the left ventricle surface, using spline interpolation, on the basis of these new control point positions. The user interface 165 of the system 100 is arranged to render a view of the template. The user may be enabled to translate and rotate the template, using the user interface 165, to obtain more views of the template. Optionally, an image unit 130 for producing an image of the template, e.g. three orthogonal projections of the template along the principal axes of the inertia tensor of the template, may be integrated into the user interface 165.

Advantageously, the system 100 may be comprised in a reporting system 300. Thus, views computed by the image unit 130 of the system 100 may be included in a medical report created by a report unit 310 together with annotations by a physician examining the image data. In an embodiment, the reporting system 300 comprises a reporting system first input connector 301 for obtaining data for the system 100 and a reporting system second input connector 302 for obtaining other data such as user annotations, patient name and age, other test and examination results, comments by a physician preparing the report, and so on. The reporting unit 310 is arranged to receive the adapted template from the system 100 and the other data from the second input 302 for preparing a report. The report is outputted via a reporting system output connector 303.

Those skilled in the art will further understand that other embodiments of the system 100 are also possible. It is possible, among other things, to redefine the units of the system and to redistribute their functions. Although the described embodiments apply to medical images, other applications of the system, not related to medical applications, are also possible.

The units of the system 100 may be implemented using a processor. Normally, their functions are performed under the control of a software program product. During execution, the software program product is normally loaded into a memory, like a RAM, and executed from there. The program may be loaded from a background memory, such as a ROM, hard disk, or magnetic and/or optical storage, or may be loaded via a network like the Internet. Optionally, an application-specific integrated circuit may provide the described functionality.

Figure 4:
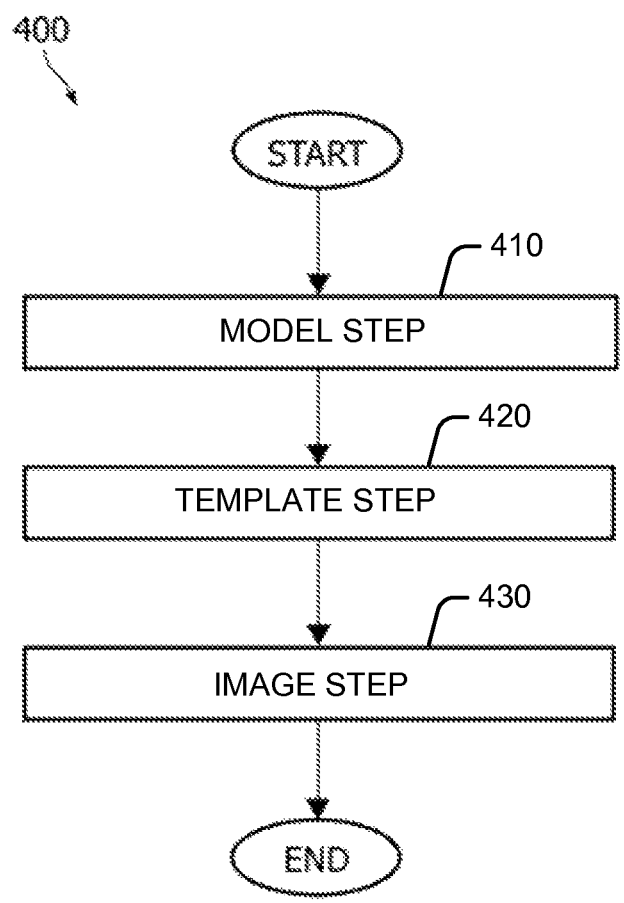
FIG. 4 shows a flowchart of an exemplary implementation of the method.

FIG. 4 shows a flowchart of an exemplary implementation of the method 400 of producing a representation of an object in image data, based on a template coupled to a model of the object. The method 400 begins with a model step 410 for adapting the model to the object in the image data. After the model step 410, the method continues to a template step 420 for adapting the template to the adapted model on the basis of the coupling between the template and the model. In the shown embodiment of the method 100, after the template step 420, the method 400 continues to an image step 430 for producing an image of the template. After the image step 430 the method 400 terminates.

A person skilled in the art may change the order of some steps or perform some steps concurrently using threading models, multi-processor systems or multiple processes without departing from the concept as intended by the present invention. Optionally, two or more steps of the method of the current invention may be combined into one step. For example, the model step 410 and the template step 420 may be combined into one adaptation step comprising a plurality of partial adaptation steps, wherein each partial adaptation step is arranged for adapting the model to the object in the image data, followed by adapting the template to the model, until a predetermined condition is fulfilled, e.g., until the number of partial adaptation steps is equal to a predetermined number. Optionally, a step of the method of the current invention may be split into a plurality of steps.

Figure 5:
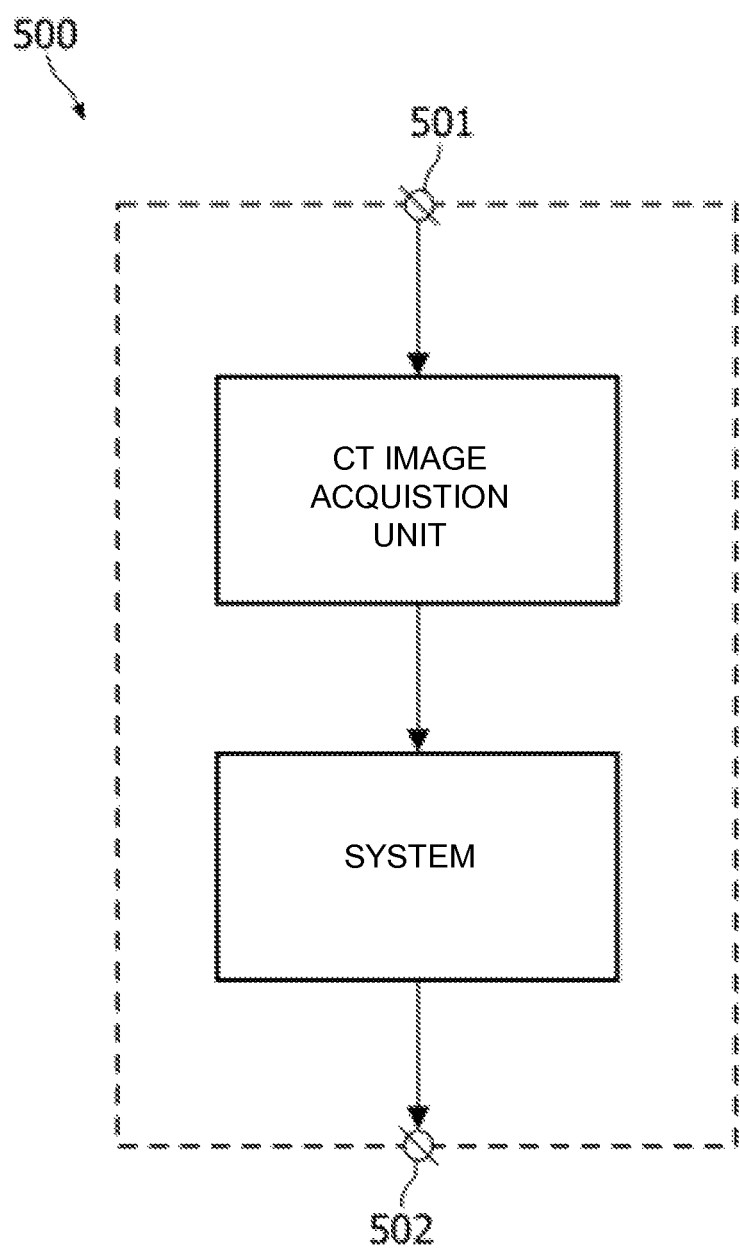
FIG. 5 schematically shows an exemplary embodiment of the image acquisition apparatus.

FIG. 5 schematically shows an exemplary embodiment of the image acquisition apparatus 500 employing the system 100, said image acquisition apparatus 500 comprising a CT image acquisition unit 510 connected via an internal connection with the system 100, an input connector 501, and an output connector 502. This arrangement advantageously increases the capabilities of the image acquisition apparatus 500, providing said image acquisition apparatus 500 with advantageous capabilities of the system 100.

Figure 6:
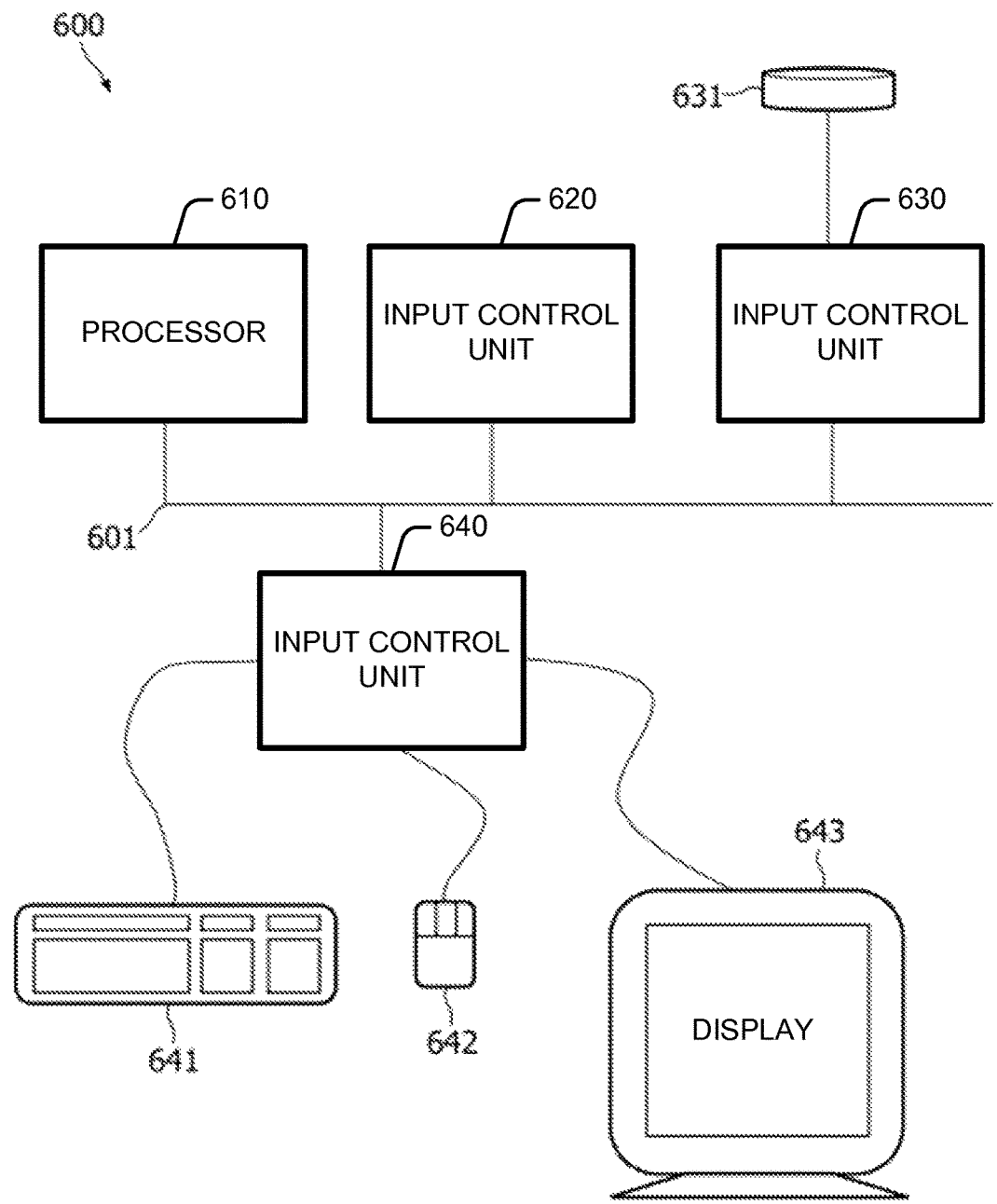
FIG. 6 schematically shows an exemplary embodiment of the workstation.

FIG. 6 schematically shows an exemplary embodiment of the workstation 600. The workstation comprises a system bus 601. A processor 610, a memory 620, a disk input/output (I/O) adapter 630, and a user interface (UI) 640 are operatively connected to the system bus 601. A disk storage device 631 is operatively coupled to the disk I/O adapter 630. A keyboard 641, a mouse 642, and a display 643 are operatively coupled to the UI 640. The system 100 of the invention, implemented as a computer program, is stored in the disk storage device 631. The workstation 600 is arranged to load the program and input data into memory 620 and execute the program on the processor 610. The user can input information to the workstation 600, using the keyboard 641 and/or the mouse 642. The workstation is arranged to output information to the display device 643 and/or to the disk 631. A person skilled in the art will understand that there are numerous other embodiments of the workstation 600 known in the art and that the present embodiment serves the purpose of illustrating the invention and must not be interpreted as limiting the invention to this particular embodiment.

It should be noted that the above-mentioned embodiments illustrate rather than limit the invention and that those skilled in the art will be able to design alternative embodiments without departing from the scope of the appended claims. In the claims, any reference signs placed between parentheses shall not be construed as limiting the claim. The word "comprising" does not exclude the presence of elements or steps not listed in a claim or in the description. The word "a" or "an" preceding an element does not exclude the presence of a plurality of such elements. The invention can be implemented by means of hardware comprising several distinct elements and by means of a programmed computer. In the system claims enumerating several units, several of these units can be embodied by one and the same item of hardware or software. The usage of the words first, second, third, etc., does not indicate any ordering. These words are to be interpreted as names.

The invention claimed is:

1. A system for producing a representation of an anatomical object in image data, based on a template coupled to a model of the object, the system comprising:
   a model unit for adapting the model to the object in the image data;
   a template unit for adapting the template to the adapted model on the basis of the coupling between the template and the model, wherein the template unit adapts the template such that a plane of the template is defined by three non co-linear points defined by features of the adapted model; and
   an image unit for producing an image of the template, wherein the image of the template comprises at least three orthogonal projections of the template along the principal axes of an inertia tensor of the template, wherein the template comprises a first portion and a second portion, and wherein the image unit is arranged for producing a first portion of the image, based on the first portion of the template, using a first visual pattern, and a second portion of the image, based on the second portion of the template, using a second visual pattern.

2. The system as claimed in claim 1, wherein the template is rigid and is movably coupled to the model.

3. The system as claimed in claim 1, wherein the template comprises a plurality of control points which are rigidly or elastically coupled to the model.

4. The system as claimed in claim 1, wherein the template is elastic.

5. The system as claimed in claim 1, wherein the template comprises at least one curve or surface.

6. A reporting system for creating a report, the reporting system comprising the system according to claim 1, the report comprising the image of the template.

7. An image acquisition apparatus comprising the system as claimed in claim 1.

8. A workstation comprising the system as claimed in claim 1.

9. A method of producing a representation of an anatomical object in image data, based on a template coupled to a model of the object, the method comprising:
   a model step for adapting the model to the object in the image data;
   a template step for adapting the template to the adapted model on the basis of the coupling between the template and the model, wherein the template step adapts the template so that a center of template is at a mass center of three non co-linear points defined by features of the adapted model; and
   an image step for producing an image of the template, wherein the image of the template comprises at least three orthogonal projections of the template along the principal axes of an inertia tensor of the template, wherein the template comprises a first portion and a second portion, and wherein a first portion of the image is produced, based on the first portion of the template, using a first visual pattern, and a second portion of the image is produced, based on the second portion of the template, using a second visual pattern.

10. The method as claimed in claim 9, further comprising: determining at least one of a position, an orientation or a shape of the template by the adapted model.

11. The method as claimed in claim 9, further comprising: determining individual characteristics of the object with respect to an external reference system.

12. The method as claimed in claim 9, wherein the template comprises a contour of the lumbar vertebra and is defined by a planar cross-section of the surface of the lumbar vertebra model and described by a plurality of control points on the surface of the model, and adapting the template to the adapted model determines new positions of the control points of the template contour on the surface model of the vertebra, which defines an adapted contour.

13. The method as claimed in claim 12, wherein the adapted contour takes into account individual characteristics of the vertebrae, including at least one of vertebral compression or fracture.

14. The method as claimed in claim 13, wherein the at least one of the vertebral compression or the fracture is not visible in the contour before the adaptation.

15. A non-transitory computer readable memory of a computer arrangement loaded with a computer program product, comprising instructions for producing a representation of an anatomical object in image data, based on a template coupled to a model of the object, the computer arrangement comprising a processing unit and the memory, the computer program product, after being loaded, providing said processing unit with the capability to carry out the tasks of:

adapting the model to the object in the image data;

adapting the template to the adapted model on the basis of the coupling between the template and the model, wherein adapting the template includes determining an axis of the template by a line obtained by applying linear regression to three non co-linear points defined by features of the adapted model; and producing an image of the template, wherein the image of the template comprises at least three orthogonal projections of the template along the principal axes of an inertia tensor of the template, wherein the template comprises a first portion and a second portion, wherein the processing unit is further provided with the capability to produce a first portion of the image, based on the first portion of the template, using a first visual pattern, and a second portion of the image, based on the second portion of the template, using a second visual pattern.

16. The computer program product of claim 15, wherein the template is rigid and is movably coupled to the model.

17. The computer program product of claim 15, wherein the template comprises a plurality of control points which are rigidly or elastically coupled to the model.

18. The computer program product of claim 15, wherein the template is elastic.

19. The computer program product of claim 15, wherein the template comprises at least one curve.

20. The computer program product of claim 15, wherein the template comprises at least one surface.

* * * * *